United States Patent [19]

Scharschmidt et al.

[11] Patent Number: 5,395,976
[45] Date of Patent: Mar. 7, 1995

[54] PROCESS FOR THE PREPARATION OF A MIXTURE OF CYCLOHEXANONE AND CYCLOHEXANOL

[75] Inventors: Jürgen Scharschmidt, Krefeld; Christine Mendoza-Frohn, Erkrath; Hans-Josef Buysch; Rainer Klotzbücher, both of Krefeld, all of Germany

[73] Assignee: Bayer Aktiengesellschaft, Leverkusen, Germany

[21] Appl. No.: 166,178

[22] Filed: Dec. 10, 1993

[30] Foreign Application Priority Data

Dec. 18, 1992 [DE] Germany ............... 42 42 2947.1

[51] Int. Cl.$^6$ .................................. C07C 45/00
[52] U.S. Cl. .............................. 568/362; 568/835
[58] Field of Search ................. 568/362, 835

[56] References Cited

U.S. PATENT DOCUMENTS

| | | | |
|---|---|---|---|
| 3,305,586 | 2/1967 | Phielix | 568/362 |
| 3,932,514 | 1/1976 | Thelen et al. | 568/362 |
| 4,162,267 | 7/1979 | Fisher et al. | 568/362 |
| 4,200,553 | 4/1980 | Van Peppen et al. | 568/362 |
| 4,407,733 | 10/1983 | Birkenstock et al. | 568/362 |
| 4,422,954 | 12/1983 | Van Peppen et al. | 568/362 |
| 4,520,129 | 5/1985 | Murtha | 568/362 |

FOREIGN PATENT DOCUMENTS

| | | | |
|---|---|---|---|
| 0012153 | 6/1980 | European Pat. Off. | |
| 1298098 | 6/1969 | Germany . | |
| 2069938 | 7/1971 | Germany | 568/362 |
| 2025726 | 2/1974 | Germany | 568/362 |
| 2045882 | 1/1976 | Germany | 568/362 |
| 242039 | 1/1987 | Germany . | |
| 6511221 | 4/1966 | Netherlands . | |
| 1063357 | 3/1967 | United Kingdom . | |

OTHER PUBLICATIONS

Noncondensed Aromatic Compounds, vol. 65, 1966, p. 5401.
Industrial Organics, vol. 107, 1987, p. 119.
Alicyclic Compounds, vol. 71, 1969, p. 389.
Alicyclic Compounds, vol. 75, 1971, p. 409.
Chemical Abstracts, vol. 76, 1972, p. 418.

*Primary Examiner*—James H. Reamer
*Attorney, Agent, or Firm*—Sprung, Horn, Kramer & Woods; William C. Gerstenzang

[57] ABSTRACT

In the hydrogenation of phenol with $H_2$ over Pd supported catalysts, the ratio of the products formed, cyclohexanone and cyclohexanol, can be predetermined by specific treatment of the catalysts during the initial activation and regeneration by $O_2$ pretreatment and $H_2$ treatment, the following time/temperature conditions being used:

a) Cyclohexanone:cyclohexanol=85:15 to 98:2
  a1) for initial activation, no $O_2$ pretreatment and $H_2$ treatment for 50–10 hours at 300°–500° C.;
  a2) for regeneration, $O_2$ pretreatment for 30–0.5 hours at 220°–380° C. and $H_2$ treatment for 2–6 hours at 150°–250° C.;

b) Cyclohexanone:cyclohexanol=30:70 to below 85:15
  b1) for initial activation, $O_2$ pretreatment for 40–3 hours at 250°–500° C. and $H_2$ treatment for 2–6 hours at 150°–250° C.;
  b2) for regeneration, $O_2$ pretreatment for 30–0.5 hours at 380°–600° C. and $H_2$ treatment for 2–6 hours at 150°–250° C.

15 Claims, No Drawings

PROCESS FOR THE PREPARATION OF A MIXTURE OF CYCLOHEXANONE AND CYCLOHEXANOL

BACKGROUND OF THE INVENTION

1. Field of the Invention

The present invention relates to a process for the preparation of cyclohexanone and cyclohexanol by hydrogenation of phenol in the gas phase over palladium on supports, which is characterized in that particular ratios of cyclohexanone to cyclohexanol can be established in a controlled manner as required by specific treatment of the catalysts during activation and regeneration.

2. Description of the Related Art

As is known, cyclohexanol is chiefly used for the preparation of adipic acid and cyclohexanone is essentially used for the synthesis of caprolactam. The two starting products in turn can be obtained by hydrogenation of phenol. If adipic acid and caprolactam production are to be supplied by this route and the two have varying capacities, it is necessary either to hydrogenate phenol exclusively to give cyclohexanol, which is achieved, for example, with certain nickel catalysts (compare Ullmann's Encyclopedia Vol. A8, page 218; DD 224315-A and DD 281079-A) and then to dehydrogenate some of the cyclohexanol, for example with catalysts of Cu, Zn or Cr (compare Ullmann's Encyclopedia Vol. A8, page 221; Chem. and Ind. 1989, page 832 and Chem. Techn. 18 (1966), page 611), or some of the phenol is hydrogenated over nickel catalysts to give cyclohexanol and another portion is hydrogenated over palladium catalysts to give cyclohexanone. Such a procedure is described, inter alia, in Chem. and Ind. 1989, page 832. In each case, two different catalysts and two plants suitable for this purpose are required.

The object was thus to prepare the two starting substances, cyclohexanone and cyclohexanol, in predetermined but variable proportions as required over only one catalyst and in only one plant.

SUMMARY OF THE INVENTION

It has now been found, surprisingly, that this object can be achieved in a simple manner if the palladium catalysts customary per se for selective hydrogenation of phenol to give cyclohexanone are activated and regenerated by particular procedures.

The present invention accordingly relates to a process for the preparation of mixtures of cyclohexanone and cyclohexanol in predetermined ratios to one another in the range from 30:70 to 98:2 by hydrogenation of phenol with hydrogen in the gas phase at 150° to 250° C. under 0.8 to 8 bar, preferably 1 to 5 bar, over supported palladium catalysts, which is characterized in that, for initial activation and for regeneration after use, the catalysts are subjected to an oxygen pretreatment, if appropriate, and then a hydrogen treatment in each case under 0.8 to 8 bar, preferably 1 to 5 bar, particularly preferably 1 to 3 bar, the following time/temperature conditions being applied to establish the predetermined ratio:

a) Cyclohexanone:cyclohexanol=85:15 to 98:2 a1) for initial activation, no $O_2$ pretreatment and $H_2$ treatment for 50–10 hours at 300°–500° C.;

a2) for regeneration, $O_2$ pretreatment for 30–0.5 hours at 220°–380° C. and $H_2$ treatment for 2–6 hours at 150°–250° C.;

b) Cyclohexanone:cyclohexanol=30:70 to below 85:15 b1) for initial activation, $O_2$ pretreatment for 40–3 hours at 250°–500° C. and $H_2$ treatment for 2–6 hours at 150°–250° C.;

b2) for regeneration, $O_2$ pretreatment for 30–0.5 hours at 380°–600° C. and $H_2$ treatment for 2–6 hours at 150°–250° C.

DETAILED DESCRIPTION OF THE INVENTION

The ratios of cyclohexanone (molecular weight 98) to cyclohexanol (molecular weight 100) are based on the weights, but because the molecular weights and other physical data lie close to one another, they also apply in a virtually identical manner to the molar or volume ratios.

This controlled and flexible adjustment of the phenol hydrogenation to various cyclohexanone/cyclohexanol mixtures was not to be expected. As a rule, cyclohexanol is quite predominantly obtained during hydrogenation over nickel catalysts, and cyclohexanone over palladium catalysts (Ullmann's Encyclopedia loc. cit.). Over palladium catalysts, a transition phase in which noticeable amounts of cyclohexanol, in addition to the main product cyclohexanone, are usually initially formed at the start of the phenol hydrogenation and decrease in the course of time, until the catalyst is "run in" (compare, for example, DD-PS 242039 page 1).

This phenomenon has been related to the slowly deactivating "hyperactive" centres initially present, which are said to be deactivated in a controlled manner by a catalyst poison employed as a moderator, such as CO (compare DD Patent 150999).

However, findings and procedures on controlled modification of palladium catalysts in respect of the object described here have not been disclosed to date.

This is achieved, however, in an unforeseeable manner by the process according to the invention.

In the publication Chem. and Ind. 1989, page 831, it is even stated and demonstrated experimentally that regenerations at elevated temperatures, such as are proposed according to the invention, are not particularly effective and lead to rapid deactivation; a similar statement is made in Chem. Techn. 29 (1977), page 41, according to which optimum activation and regeneration are said to take place at 170°–185° C.

Suitable starting substances for the process according to the invention are phenol and hydrogen. The phenol must have a particular purity such as usually exists in phenol qualities obtained by the so-called Hock process. In particular, catalyst poisons, such as compounds of nitrogen, sulphur and mercury, and also CO and CO generators, such as formic and oxalic acid, should not be present in the phenol or should be present only in small amounts of less than 10 ppm, preferably less than 1 ppm, and more preferably still should not be detectable if larger amounts of cyclohexanol are expected in the mixtures to be prepared. However, if a particularly high selectivity for cyclohexanone is to be achieved, traces of sulphur compounds or CO or CO generators, preferably CO or CO generators, can be added in the range from 2 to 150, preferably 10 to 100 ppm (compare DD Patent 150999 and U.S. Pat. No. 4,520,129).

Restrictions similar to those for phenol apply to hydrogen. The abovementioned catalyst poisons may be present only in the limits mentioned, but preferably are no longer detectable. Nevertheless, inert gases, such as hydrocarbons, nitrogen, noble gases or carbon dioxide, may be entirely acceptable. For economic reasons, however, it may be appropriate to eliminate such concomitant substances, since they must be removed regularly from the stream of circulating gas, together with large quantities of hydrogen in each case, which then have to be removed, if appropriate. Hydrogen is employed in an amount of 3–30 tool/tool of phenol, preferably 3.5–10 mol/mol.

Cyclohexanol and/or cyclohexanone can also be admixed to the phenol and hydrogen, depending on which of the products has been formed in excess and is not currently being utilized, but can be converted into the particular product required by recycling.

Palladium catalysts which are suitable for the process according to the invention are those which are usually used for hydrogenation of phenol to give cyclohexanone, that is to say catalysts which contain palladium deposited on known supports.

Suitable catalysts are, for example, those such as are described in DE-A 1 298 098, DE-A 2 059 938, DE-A 2 025 726, DE-A 1 290 538, DD 150 999, DD 92 243, EP 12 153, DE-A 2 606 489, DE-B 2 045 882, DE-A 1 952 208, DE-A 2 025 726, Chem. and Ind. 1989, pages 830-2 and Chem. Techn. 29 (1977), pages 38–41. Particularly suitable catalysts are those which contain support materials from the group comprising aluminium oxides, preferably $\gamma$-$Al_2O_3$, boehmite or $\alpha$-$Al_2O_3$, silicon dioxides, silicon dioxide/aluminium oxide mixtures, in particular alumosilicates, amorphous silicic acids, kieselguhrs, carbonates of barium, strontium, calcium and magnesium, mixtures of these compounds, if appropriate with addition of oxides of silicon or aluminium, magnesium oxides, titanium oxides, zirconium oxides, magnesium silicates, zirconium silicates and spinels of alkali metal and alkaline earth metal aluminates, preferably those based on lithium and barium. Those catalysts which have been prepared using alkali metal and alkaline earth metal bases and in which palladium is present in concentrated form in the form of a shell in the outer layer of the support are preferred.

The palladium, which is applied to the support in accordance with the references mentioned, can additionally contain other noble metals, such as platinum, rhodium, iridium or ruthenium, in amounts of up to 20% by weight, preferably up to 10% by weight; however, palladium is particularly preferably used by itself.

The catalysts can be used in the most diverse forms, for example as beads, granules, extrudates, tablets, saddles, Raschig rings, fragments or honeycomb ceramic.

The catalyst must be activated before carrying out the phenol hydrogenation. This is effected, if high selectivities for cyclohexanone are desired, that is to say mixtures of cyclohexanone to cyclohexanol of 85:15 to 98:2, by treating the catalyst with hydrogen-containing gases, in particular hydrogen/nitrogen mixtures, or with pure hydrogen for 50–10 hours at 300°–500° C., preferably 40–20 hours at 350°–450° C., particularly preferably 35–20 hours at 370°–450° C. The result of this activation is particularly surprising, since the run-in time otherwise customary is shortened considerably according to the invention compared with the run-in time with the activation at about 180° C. recommended in the literature.

After deactivation caused by use, the catalyst is regenerated by passing over it inert gas (for example nitrogen)/oxygen mixtures, depending on the extent of coking, for 30–0.5 hours at 220°–380° C., preferably for 25–1 hours at 230°–370° C., particularly preferably for 20–1 hours at 250°–360° C., the oxygen content in the mixture being increased slowly from, where appropriate, less than 1% by volume, for example 0.5% by volume, depending on the amount of organic deposits to be burned off and the possibilities for removing the heat of combustion, up to 30% by volume, preferably to the content of 21% by volume of atmospheric air. Accordingly, for this purpose, atmospheric air can first be diluted to 0.5% by volume of $O_2$ with inert gas (for example $N_2$), and this dilution can be reduced by decreasing the inert gas content, until the normal content of about 21% by volume is reached. To achieve up to 30 % by volume of $O_2$, atmospheric air can be enriched with $O_2$.

On the other hand, if mixtures with higher contents of cyclohexanol are desired, that is to say more than 15% to 70%, the activation of the palladium catalyst is first carried out by passing over oxygen/nitrogen mixtures with oxygen contents of up to 21% by volume, and if appropriate even higher, for 40–3 hours at 250°–500° C., preferably for 30–4 hours at 300°–450° C., particularly preferably for 24–5 hours at 350°–425° C., and then by passing over hydrogen-containing gases or pure hydrogen at 150°–250° C. for 2–6 hours.

The regeneration of a deactivated catalyst which is to produce high cyclohexanol contents is carried out by passing over oxygen/nitrogen mixtures, depending on the circumstances of whether a large quantity of or little organic substance has been deposited, with oxygen contents of less than 1% by volume up to those of 21% by volume or even higher, which can be approached slowly in the regeneration process, for 30–0.5 hours at 380°–600° C., preferably for 25–1 hours at 390°–580° C., particularly preferably for 20–1 hours at 400°–550° C., and then by passing over hydrogen-containing gases or pure hydrogen at temperatures of 150° to 250° C. in the course of 2–6 hours.

The $O_2$ pretreatment and the $H_2$ treatment are carried out under a pressure of 0.8 to 8 bar, preferably 1 to 5 bar, particularly preferably 1 to 3 bar.

These pressure data in each case relate to the total pressure of the $O_2$/inert gas or $H_2$/inert gas mixtures.

The initial activation according to the invention and the regenerations caused by use can of course be carried out in a separate reaction vessel. However, the full economic benefit is achieved if these treatment operations are carried out in the hydrogenation reactor for the preparation of the cyclohexanone/cyclohexanol mixture. Such reactors are those which are known to the expert, such as fixed bed reactors, in which the catalyst is arranged in tubes or on trays, if appropriate mixed with inert packing, or fluidized bed reactors.

Before the start of the $H_2$ treatment, the oxygen of the preceding $O_2$ pretreatment is displaced completely by non-combustible inert gases, such as are employed for mixing the $O_2$ (for example $N_2$, $CO_2$ or noble gases).

The $H_2$ treatment which follows in the context of regeneration can be carried out as a separate step. Preferably, the $H_2$ treatment is carried out under hydrogenation operating conditions, that is to say simultaneously with the resumption of phenol hydrogenation.

The phenol hydrogenation is carried out at 150° to 250° C. and 0.8 to 8 bar, preferably 1 to 5 bar.

EXAMPLES

Example 1a (not according to the invention)

Preparation of the catalyst

Impregnation of Li-Al spinel with $Na_2PdCl_4$ (18 g/l), reduction with hydrazine, washing, drying (according to Example 1a from DE-B 2 045 882).

Example 1b (not according to the invention)

The catalyst obtained according to Example 1a was employed in a technical plant for the preparation of cyclohexanone, phenol conversions of >99.9% being achieved. After a running time of about 6,000 hours, the phenol content in the crude product rose to more than 1,000 ppm. The production was interrupted to take samples of the deactivated catalyst. During the second period of its running time, it produced a cyclohexanone/- cyclohexanol ratio of 16:1 (see Example 1b of DE- 2 045 882).

Example 1c (according to the invention)

The catalyst from Example 1a was reduced in a mixture of 10% of $H_2$ and 90% of $N_2$ (% by volume) for 24 hours at 400° C. and then loaded with 1.0 g of phenol/ml of catalyst×hour and 4 mol of hydrogen/mole of phenol at 150° C. Cyclohexanone and cyclohexanol were obtained in a ratio of 12.0:1 with complete conversion of the phenol and a selectivity of 99.8%.

After a running time of 600 hours at a cyclohexanone/- cyclohexanol ratio which remained practically constant, the experiment was discontinued.

This experiment demonstrates that by a particular pretreatment of the fresh catalyst with hydrogen-containing gases, in contrast to the prior art (see DE-B 2 045 882, Examples 1a and 1b), a particular different ratio of cyclohexanone to cyclohexanol can be established.

Example 2 (according to the invention)

The catalyst from Example 1a was heated for 16 hours at 350° C. in a stream of air and, after the air had been displaced, was reduced at 150° C. with nitrogen/hydrogen (90:10 by volume) for 4 hours and when loaded with 1.0 g of phenol/ml of catalyst×hour and 4 tool of hydrogen/mole of phenol at 150° C. Cyclohexanone and cyclohexanol were obtained in a ratio of 1.5 with complete conversion of the phenol and a selectivity of 99.9%. Even with a lower loading of about 0.7 g of phenol/ml of catalyst×hour, the value dropped only insignificantly from 1.5 to 1.3. After a running time of 600 hours with the cyclohexanone/cyclohexanol ratio remaining practically constant, the experiment was discontinued.

This experiment demonstrates that a particular pretreatment of the fresh catalyst with oxygen-containing gases can establish a particular ratio of cyclohexanone to cyclohexanol. Comparison with Example 1 reveals that adjustment to various product compositions is possible from the same contact catalyst, depending on the pretreatment.

Example 3a (not according to the invention)

An $\alpha$-$Al_2O_3$ support (SPH 512, Rhône-Poulenc) was impregnated with NaOH, dried, subsequently impregnated with $Na_2PdCl_4$, reduced with hydrazine, washed and dried. The Pd deposit was 18 g/l of catalyst (according to Example 1a from DE-AS 2 045 882).

Example 3b (according to the invention)

The catalyst from Example 3a was reduced for 24 hours at 400° C. in a mixture of 10% of $H_2$ and 90% of $N_2$ (% by volume) and then loaded with 1.0 g of phenol/ml of catalyst×hour and 4 mol of hydrogen/mole of phenol at 150° C. After a running time of only 100 hours, cyclohexanone and cyclohexanol were obtained in a ratio of 47:1 with complete conversion of the phenol and a selectivity of 99.9%.

After a running time of 600 h with the cyclohexanone/- cyclohexanol ratio remaining practically constant, the experiment was discontinued.

This experiment demonstrates that a particular ratio of cyclohexanone to cyclohexanol can be established by a particular pretreatment of the fresh catalyst with hydrogen-containing gases (compare Example 1c and DE-B 2 045 882, Example 1a and 1b).

Example 4

The catalyst from Example 3a was treated for 24 hours at 400° C. in air and then loaded with 1.0 g of phenol/ml of catalyst×hour and 4 mol of hydrogen/mole of phenol at 150° C. Cyclohexanone and cyclohexanol were obtained in a ratio of 3:1 with complete conversion of the phenol and a selectivity of 99.8%.

After a running time of 600 hours with the cyclohexanone/cyclohexanol ratio remaining practically constant, the experiment was discontinued.

This experiment demonstrates that a particular ratio of cyclohexanone to cyclohexanol can be established by a particular pretreatment of fresh catalyst with oxygen-containing gases.

Comparison with Example 3 reveals that adjustment to various product compositions is possible from the same contact catalyst, depending on the pretreatment.

Example 5 (according to the invention)

After a running time of 6,000 hours, the catalyst from Example 1b was regenerated by passing over air at 350° C. for 4 hours and, after the air had been displaced, was subsequently reduced with nitrogen/hydrogen (90:10 by volume) at 150° C. for 4 hours. Under a loading of 1.0 g of phenol/ml of catalyst×hour at a temperature of 150° C. and a molar ratio of hydrogen to phenol of 4:1, the regenerated contact catalyst produced a conversion of about 97%, a selectivity of 99.9 to 99.98% and, after a run-in time of about 200 hours, a reaction product having a cyclohexanone/cyclohexanol ratio of 16 to 18. After a running time of 2,800 hours, the experiment was ended with practically unchanged results.

This experiment shows that even after a short run-in time, the desired high product ratio of cyclohexanone to cyclohexanol and moreover a long running time are achieved with very little formation of by-products by the regeneration according to the invention.

Example 6 (according to the invention)

After a running time of 6,000 hours, the catalyst from Example 1b was regenerated by passing over air at 500° C. for 4 hours and, after the air had been displaced by nitrogen, was subsequently reduced at 150° C. for 4 hours with a mixture of 10% of $H_2$/90% of $N_2$.

Under a loading of 0.9 g of phenol/ml of catalyst×hour at a reaction temperature of 150° C. and a molar ratio of hydrogen to phenol of 4.5: 1, complete conversion, a selectivity of 99.7 to 99.8% and a ratio of cyclohexanone to cyclohexanol of 2.2 to 2.4 were obtained without a substantial change over a running time of 600 hours.

Comparison with Example 5 reveals that adjustment to various product compositions is possible from the same deactivated contact catalyst, depending on the regeneration conditions.

Example 7a (not according to the invention)

A ceramic support with 98% of α-$Al_2O_3$ and 2% of MgO (Hoechst-Ceram Tec, A 980) was impregnated with a Ba salt, dried and calcined, so that a Ba spinel containing 6.5% of Ba was formed.

This Ba spinel was impregnated with sodium hydroxide solution according to Example 1a from DE-AS 2 045 882, dried, impregnated with $Na_2PdCl_4$, reduced with hydrazine, washed and dried. The finished catalyst has a content of 8 g/l of Pd.

Example 7b (not according to the invention)

The catalyst obtained according to 7a was employed for the preparation of cyclohexanone in a pilot plant (11 tube reactor of 4 cm diameter), phenol conversions of >99.9% being achieved. After a running time of 2,170 hours, the phenol content in the crude product rose to more than 1,000 ppm. The experiment was interrupted to take samples of the deactivated catalyst.

Example 7c (according to the invention)

The catalyst from Example 7b was regenerated by passing over air at 350° C. for 4 hours and, after the air had been displaced by nitrogen, was reduced by passing over 10% of hydrogen/90% of $N_2$ at 150° C. for 4 hours. Hydrogen and phenol in a molar ratio of 4:1 were passed over the catalyst at 150° C. under a loading of 1.0 g of phenol/ml of catalyst×hour. After a run-in time of 150 hours, a cyclohexanone/cyclohexanol ratio of 18 to 30 was obtained at a conversion of 95 to 97% and a selectivity of 99.7 to 99.9%. The experiment was discontinued after 2,600 hours (cf. comment on Example 5).

Example 8a (not according to the invention)

The catalyst obtained according to 3a was employed for the preparation of cyclohexanone in a pilot plant (11 tube reactor of 4 cm diameter), phenol conversions of >99.9% being achieved. After a running time of 900 hours, the phenol content in the crude product rose to more than 1,000 ppm. The experiment was interrupted to take samples of the deactivated catalyst.

Example 8b (according to the invention)

The catalyst from Example 8a was regenerated by passing over air at 500° C. for 16 hours and, after the air had been displaced by nitrogen, was reduced by passing over a mixture of 10% by volume of $H_2$ and 90% of $N_2$ at 150° C. for 4 hours.

Hydrogen and phenol were then passed over the catalyst in a molar ratio of 4:1 at 150° C. and under a loading of 1.0 g of phenol/ml of catalyst×hour: After a run-in time of 150 hours, a cyclohexanone/cyclohexanol ratio of 4:1 was obtained at a conversion of 99.9% and a selectivity of 99.9%. After 600 hours, the experiment was discontinued (compare comment on Example 6).

Example 9 (according to the invention)

After 6,000 hours, the catalyst from Example 1b was regenerated by passing over air at 270° C. for 4 hours and, after the air had been displaced by nitrogen, was reduced with 10% of hydrogen/90% of $N_2$ at 150° C. in the course of 4 hours. Hydrogen and phenol were passed over in a molar ratio of 4:1 under a loading of 1 g of phenol/ml of catalyst×hour at 150° C. Because of the relatively low regeneration temperature and relatively short regenerating time, the ran-in time of the catalyst increased to 500 hours, a cyclohexanone/cyclohexanol ratio of 1.3 to 8 existing. A cyclohexanone/cyclohexanol ratio of 19 to 21 was then reached at a conversion of 98 to 99% and a selectivity of 99.7 to 99.8%. After 2,600 hours, the experiment was discontinued with practically unchanged values.

Example 10 (Comparison Example)

The catalyst from Example 1b was regenerated by passing over air at 185° C. for 6 hours and, after the air had been displaced by nitrogen, was reduced by passing over a mixture of 10% by volume of $H_2$ and 90% of $N_2$ at 150° C. for 4 hours.

Hydrogen and phenol were then passed over the catalyst in a molar ratio of 4:1 at 150° C. and under a loading of 1.0 g of phenol/ml of catalyst×hour. A conversion of only 97% and a cyclohexanone/cyclohexanol ratio of 4:1 at a selectivity of 99.9% were obtained. The experiment was discontinued after 600 hours.

This experiment reveals that 185° C., corresponding to the prior art (Chem. Techn. 29 (1977) page 41) is unsuitable as a regenerating temperature for converting the catalyst back into its previous state (see Example 1b). In that example, a conversion of 99.9% and a cyclohexanone/cyclohexanol ratio of 19:1 was achieved.

What is claimed is:

1. A process for the preparation of mixtures of cyclohexanone and cyclohexanol in predetermined ratios to one another in the range from 30:70 to 98:2 by hydrogenation of phenol with hydrogen in the gas phase at 150 to 250° C. under 0.8 to 8 bar over a supported palladium catalyst, wherein, for initial activation and for regeneration after use, the catalyst is subjected to an oxygen pretreatment, if appropriate, and then a hydrogen treatment in each case under 0.8 to 8 bar, the following time/temperature conditions being applied to establish the predetermined ratio:
   a) Cyclohexanone: cyclohexanol=85.15 to 98.2
      a1) for initial activation, no $O_2$ pretreatment and $H_2$ treatment for 50-10 hours at 300°-500° C.;
      a2) for regeneration, $O_2$ pretreatment for 30-0.5 hours at 220°-380° C. and $H_2$ treatment for 2-6 hours at 150°-250° C.;
   b) Cyclohexanone:cyclohexanol=30:70 to below 85:15
      b1) for initial activation, $O_2$ pretreatment for 40-3 hours at 250°-500° C. and $H_2$ treatment for 2-6 hours at 150°-250° C.;
      b2) for regeneration, $O_2$ pretreatment for 30-0.5 hours at 380°-600° C. and $H_2$ treatment for 2-6 hours at 150°-250° C.

2. The process of claim 1, wherein phenol is hydrogenated with hydrogen under 1 to 5 bar.

3. The process of claim 1, wherein the catalyst, for initial activation and for regeneration after use, is subjected to a hydrogen treatment in each case under 1 to 5 bar.

4. The process of claim 3, wherein the catalyst, for initial activation and for regeneration after use, is subjected to a hydrogen treatment in each case under 1 to 3 bar.

5. The process of claim 1, wherein an inert gas/$O_2$ mixture, the $O_2$ content of which is initially 0.5% by volume and increases to 30% by volume during the $O_2$ treatment is employed for the $O_2$ treatment.

6. The process of claim 5, wherein the $O_2$ content rises to up to 21% by volume.

7. The process of claim 6, wherein atmospheric air is first diluted with inert gas and, during the $O_2$ treatment, the inert gas content is reduced until the normal value of 21% by volume of $O_2$ is reached.

8. The process of claim 1, wherein the $O_2$ pretreatment and the $H_2$ treatment are carried out in the phenol hydrogenation reactor.

9. The process of claim 8, wherein the $H_2$ treatment is carried out in the context of regeneration under the hydrogenation operating conditions.

10. The process of claim 1, wherein, to achieve cyclohexanon/cyclohexanol ratios of 85:15 to 98:2, the initial activation is carried out by $H_2$ treatment for 40 to 20 hours at 350° to 450° C. and the regeneration is carried out by $O_2$ treatment for 25 to 1 hours at 230° to 370° C. and subsequent $H_2$ treatment.

11. The process of claim 10, wherein the initial activation is carried out by $H_2$ treatment for 35 to 20 hours at 370° to 450° C.

12. The process of claim 10, wherein the regeneration is carried out by $O_2$ treatment for 20 to 1 hours at 250° to 360° C. and subsequent $H_2$ treatment.

13. The process of claim 1, wherein to achieve cyclohexanone/cyclohexanol ratios of 30:70 to below 85:15, the initial activation is carried out by $O_2$ treatment for 30 to 4 hours at 300° to 450° C. and subsequent $H_2$ treatment and the regeneration is carried out by $O_2$ treatment for 25 to 1 hours at 390° to 580° C. and subsequent $H_2$ treatment.

14. The process of claim 13, wherein the initial activation is carried out by $O_2$ treatment for 24 to 5 hours at 350°–425° C. and subsequently $H_2$ treatment.

15. The process of claim 13, wherein the regeneration is carried out by $O_2$ treatment for 20 to 1 hours at 400° to 550° C. and subsequent $H_2$ treatment.

* * * * *

UNITED STATES PATENT AND TRADEMARK OFFICE
CERTIFICATE OF CORRECTION

PATENT NO. : 5,395,976

DATED : March 7, 1995

INVENTOR(S) : Scharschmidt, et al.

It is certified that error appears in the above-identified patent and that said Letters Patent is hereby corrected as shown below:

Title Page     [30] Foreign Application Priority Date: After " Germany... " delete " 42 42 2947.1 " and substitute -- 42 42 947.1 --

Title Page     FOREIGN PATENT DOCUMENTS: Delete " 2069938 " and substitute -- 2059938 --

Signed and Sealed this

Twenty-third Day of May, 1995

*Attest:*

BRUCE LEHMAN

*Attesting Officer*     *Commissioner of Patents and Trademarks*